United States Patent
Torrance et al.

(10) Patent No.: US 8,394,078 B2
(45) Date of Patent: Mar. 12, 2013

(54) INTERVENTIONAL CATHETERS INCORPORATING AN ACTIVE ASPIRATION SYSTEM

(75) Inventors: Casey Torrance, Seattle, WA (US); Jared Salstrom, Renton, WA (US)

(73) Assignee: MEDRAD, Inc., Indianola, PA (US)

( * ) Notice: Subject to any disclaimer, the term of this patent is extended or adjusted under 35 U.S.C. 154(b) by 0 days.

(21) Appl. No.: 12/776,269

(22) Filed: May 7, 2010

(65) Prior Publication Data
US 2011/0118660 A1 May 19, 2011

Related U.S. Application Data

(63) Continuation-in-part of application No. 11/866,975, filed on Oct. 3, 2007, now Pat. No. 7,713,235.

(60) Provisional application No. 60/894,173, filed on Mar. 9, 2007, provisional application No. 60/828,209, filed on Oct. 4, 2006.

(51) Int. Cl.
*A61M 25/00* (2006.01)
(52) U.S. Cl. ............ 604/528; 604/22; 606/169; 606/180
(58) Field of Classification Search ............... 604/19, 604/21–22, 35, 528; 606/159, 169–171, 606/180
See application file for complete search history.

(56) References Cited

U.S. PATENT DOCUMENTS

| 5,284,486 | A | 2/1994 | Kotula et al. |
| 5,569,275 | A | 10/1996 | Kotula et al. |
| 5,681,336 | A * | 10/1997 | Clement et al. ............... 606/159 |
| 6,001,112 | A | 12/1999 | Taylor |
| 6,063,069 | A | 5/2000 | Cragg et al. |
| 6,126,667 | A * | 10/2000 | Barry et al. .................. 606/159 |
| 6,206,898 | B1 | 3/2001 | Honeycutt et al. |
| 6,451,036 | B1 | 9/2002 | Heitzmann et al. |
| 6,482,216 | B1 * | 11/2002 | Hiblar et al. ................. 606/159 |
| 6,503,261 | B1 | 1/2003 | Bruneau et al. |
| 6,565,588 | B1 | 5/2003 | Clement et al. |
| 6,666,874 | B2 | 12/2003 | Heitzmann et al. |
| 6,692,482 | B2 * | 2/2004 | Heller et al. ................. 604/528 |
| 2007/0060888 | A1 | 3/2007 | Goff et al. |
| 2008/0103446 | A1 | 5/2008 | Torrance et al. |

FOREIGN PATENT DOCUMENTS

| WO | 9521576 A1 | 8/1995 |
| WO | 2004080345 A2 | 9/2004 |
| WO | 2004080507 A2 | 9/2004 |

* cited by examiner

*Primary Examiner* — Quynh-Nhu H Vu
(74) *Attorney, Agent, or Firm* — Speckman Law Group PLLC; Ann W. Speckman

(57) ABSTRACT

An interventional catheter assembly comprises an operating head for removing obstructive material from a target site in a body lumen or cavity and at least one aspiration port located proximal to the operating head and penetrating the catheter assembly, the aspiration port being in communication with a sealed lumen that communicates with a vacuum system for withdrawing aspirate fluid and obstructive material from the target site. The interventional catheter incorporates an elongated guidewire lumen bushing extending proximally from a distal region of the operating head to reduce the clearance between the guidewire and the internal surface of the guidewire lumen during operation of the interventional catheter. This feature restricts entry of fluid and debris into the guidewire lumen and promotes maintenance of consistent and high aspiration pressure and volume during operation of the aspiration system and interventional catheter assembly.

16 Claims, 6 Drawing Sheets

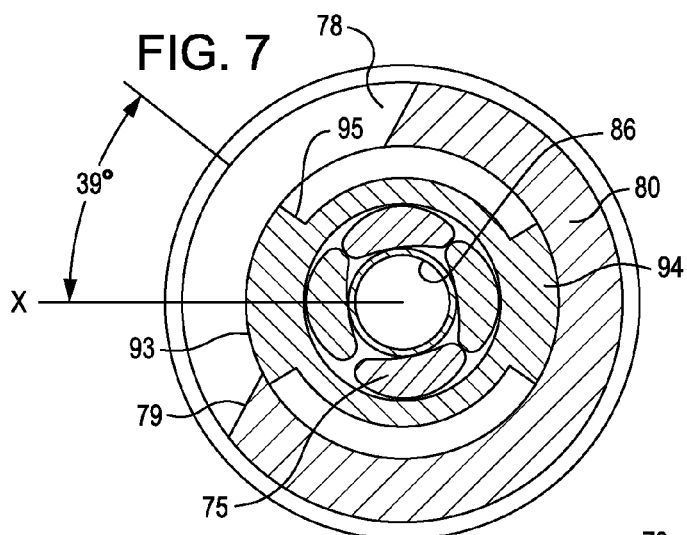
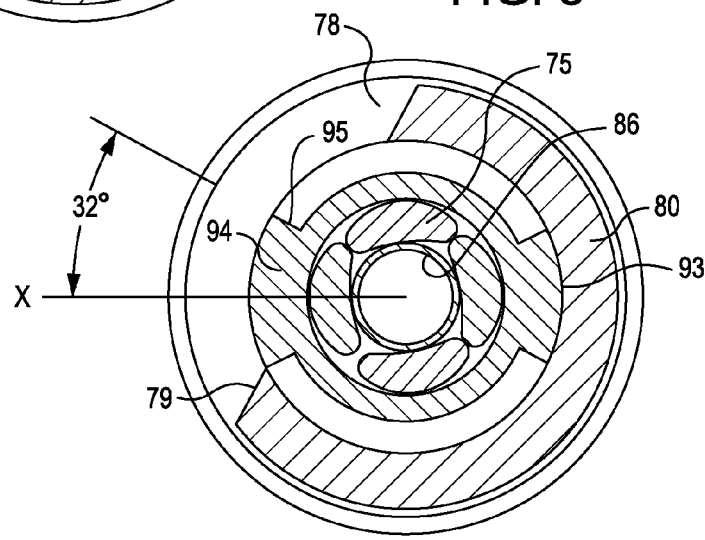
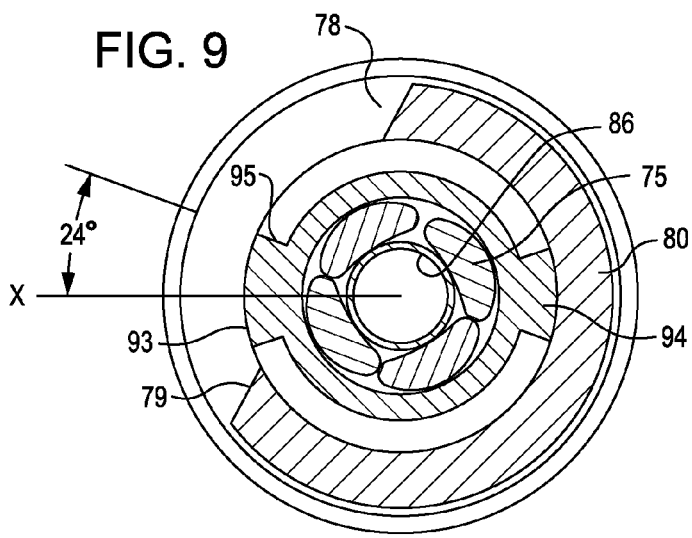

INTERVENTIONAL CATHETERS INCORPORATING AN ACTIVE ASPIRATION SYSTEM

REFERENCE TO PRIORITY APPLICATIONS

This application is a continuation-in-part of U.S. patent application Ser. No. 11/866,975, filed Oct. 3, 2007, and issued as U.S. Pat. No. 7,713,235 on May 11, 2010, which claims priority to U.S. Provisional Patent Application Nos. 60/894,173 filed Mar. 9, 2007, and 60/828,209 filed Oct. 4, 2006. The disclosures of these priority applications are incorporated by reference herein in their entireties.

FIELD OF THE INVENTION

The present invention relates to systems and methods for removing material, such as obstructions and partial obstructions, from an internal lumen or cavity of a mammalian subject, such as a blood vessel. More particularly, the present invention relates to interventional catheters having an operating head incorporating a device for removing obstructions and partial obstructions from a lumen or cavity, and an active aspiration system for removal of fluids and debris cleared from the target site.

BACKGROUND OF THE INVENTION

Removal of disease such as atherosclerotic plaque, thrombus and other types of obstructions and partial obstructions from internal body lumens or cavities using advanceable, rotating operating heads is a well-established interventional technique. Numerous interventional catheters have been conceived and developed. Most of these systems require placement of a guiding catheter and guide wire prior to introduction of the interventional catheter and placement of the interventional catheter at the target operating site. Many of these prior art systems incorporate mechanical aspiration systems to remove the ablated material from the site and some systems incorporate, or are used in conjunction with, other mechanisms such as distal filters for preventing removed material from circulating in the blood stream.

In interventional catheters that employ a "cutting head," cutter structures must be benign during navigation of the operating head to and from the interventional target site, yet effectively remove material during the operation. In addition, cutter structures must effectively remove diseased, or undesired, material without damaging delicate neighboring tissue, such as blood vessel walls or other healthy tissue, which often surrounds and may be attached to the undesired material. Thus, it is important for cutter structures of interventional catheters to accurately and reliably differentiate between the diseased material and healthy tissue.

Differential cutting blades exert high shear forces against relatively hard substrates to cut or ablate relatively hard, inelastic, material. Softer, elastic structures, such as healthy tissue, blood vessel walls and the like, are deformed rather than cut by differential cutting blades, thereby reducing the shear forces and protecting elastic structures from damage. Less elastic material does not deform when contacted by a differential cutting blade, and shear stresses are consequently exerted on less elastic material to cut or scrape and ablate the material without damaging elastic tissue in proximity. In this manner, fragments of diseased, undesirable material are removed by differential cutting blades, while the more elastic, healthy tissue remains undamaged.

U.S. Pat. No. 4,445,509 describes differential cutting in the context of an atherectomy device. This patent describes a cutter assembly having a plurality of cutting flutes, each cutting flute having a blade surface operating according to the principle of differential cutting. Aspiration ports are provided in the body of the cutter assembly for collection and removal of particulates and liquids from the site of the intervention. U.S. Pat. Nos. 6,565,588 and 6,818,001, together with U.S. Patent Publication 2004/0006358 A1, also disclose the use of cutter assemblies to separate undesired material from underlying tissue at a site of intervention, with an aspiration system incorporating aspiration ports provided between the cutting surfaces for withdrawal of liquids and particulate debris from the site.

Some interventional catheters use diamond grit on a cutting surface in an effort to provide highly divided, small particle size debris. Relatively coarse diamond grit is more likely to damage elastic, healthy tissue such as blood vessel walls. Relatively fine diamond grit has slow material removal rates, requiring the use of higher rotational speeds. The use of grit or abrasive particles or surfaces can, however, be beneficial and generate small particulate debris, providing effective material removal.

Alternative material removal systems may incorporate an Archimedes screw-type mechanism at a distal end of an interventional catheter, in which material is caught between the threads of the screw and withdrawn from the site using mechanical rotational motion. Material removal systems may also incorporate a plaque excision device having a blade that traverses and exits a window at a distal end of an interventional catheter to scrape plaque from a vessel wall and collect it in an internal collection space provided in the distal end of the interventional catheter.

In any of these material removal systems, removal of debris generated at the site of intervention is critical to prevent distal embolization of the debris. Several prior art interventional catheters provide for aspiration of liquids and/or debris from the material removal site. Aspirating thrombectomy catheters employ a catheter having a vacuum system to draw thrombus into the catheter and remove it from the site. Many interventional catheters incorporate, or are used with, a distal filter mechanism that traps debris before it can be carried away in the bloodstream. Numerous interventional catheters also provide infusion of a liquid to the site of the intervention. Infused liquids may assist in the material removal process, or may be provided as diagnostic or therapeutic materials prior to, during or following an intervention.

Despite the many and varied approaches to material removal from lumens such as blood vessels and the availability of many and varied material removal systems, challenges remain in providing systems for removing material from a lumen, such as a blood vessel, safely, reliably and effectively, without causing complications. The safety and reliability of the system is manifestly critical. Recovery of debris generated during a material removal operation, or breaking down the debris to a particle size that will not produce blood vessel damage or embolic events, is essential.

SUMMARY OF INVENTION

The present invention provides interventional catheters that may be employed to rapidly and effectively remove unwanted material from body lumens or cavities. Interventional catheters and control systems disclosed herein may be adapted for use within a variety of body lumens or cavities such as blood vessels and vascular cavities, gastrointestinal cavities, lumens or cavities in the urinary system and in male and female reproductive organs, and other fluid cavities such as pulmonary lumens and gas exchange cavities, nasal and sinus cavities and the like. The lumen or cavity may form a generally tubular structure, such as a blood vessel, a ureter, a fallopian tube, a nasal passageway, and other tubular passageways. For example, systems of the present invention may be used for removing undesired material from native blood vessels such as native coronary, renal, cranial, peripheral and other blood vessels, artificial or grafted vessels such as saphenous vein grafts, and the like. The lumen may have implanted devices, such as stents, in place. The lumen or cavity may be within, or in proximity to, an organ such as a kidney, gall bladder, lung or the like, or the body cavity may form part of another system, such as a lymph node, spinal canal or the like. Interventional catheters are generally used to remove unwanted material from a target site in body lumens or cavities of mammalian subjects, particularly human patients.

The undesired material that is removed using interventional catheter assemblies and control systems disclosed herein may be disease material such as atherosclerotic plaque, calcified plaque, thrombus, or other types of deposits, gallstones, a valve or portion thereof, and the like. In certain embodiments, the interventional catheter assemblies disclosed herein are employed in the treatment of cardiovascular or peripheral artery disease (PAD) to remove disease material from blood vessels, including peripheral blood vessels. The present interventional catheter assembly includes a catheter system that is at least partially inserted and navigated within a patient's body while an operator controls the system externally of the catheter system. The interventional catheters disclosed herein incorporate a material removal component, referred to herein as an "operating head," which is generally positioned at or near the distal end of the interventional catheter system. As used herein, "proximal" refers to a direction toward the system controls and the operator along the path of the drive shaft and catheter system, and "distal" refers to the direction away from the system controls and the operator along the path of the drive shaft and catheter system toward or beyond a terminal end of the operating head.

Fluidic communication between the operating head and externally positioned components of the interventional catheter system is generally provided by one or more sealed passageways of the catheter system. Other types of communication systems or pathways may also be provided for delivery of power, for rotationally driving and translating the operating head, for implementing various control features, and the like. The operating head may be driven, or controlled, using electrical systems, radio frequency and other remote control systems, mechanical systems, magnetic systems and other systems or modalities suitable for remote operation of an operating head. The operating head may also incorporate features providing additional functionalities such as ultrasound guidance and imaging systems and the like. The system components described below are described as exemplary components and are not intended to limit the scope of the invention.

The interventional catheter system may be provided with a guidewire bore and be used in conjunction with a flexible guidewire that is navigated through internal pathways, such as blood vessels, to a target material removal site. For partial obstructions, the guidewire is generally placed across the lesion and the operating head of the interventional catheter is advanced on the guidewire to the target site and then into and through the lesion. When a lumen is totally obstructed and a guidewire cannot penetrate the obstruction without causing harm to nearby tissue or risking embolization, the operating head may be advanced beyond the distal tip of the guidewire and into and through the obstruction, or the operating head and guidewire may be advanced in tandem. Other methods that may be employed for guiding and steering the operating head include, but are not limited to, radio frequency systems, stereotactic systems, magnetic systems, remote control systems, and the like. The interventional catheters disclosed herein may be adapted for use with any of these steering systems.

The operating head may take any of a variety of forms. In one embodiment, the operating head is rotatable, incorporates cutter elements, and is operably connected to a rotatable and axially translatable drive shaft and catheter system, a drive system and control systems, and comprises at least one distally located cutter assembly, wherein the cutter assembly includes at least one cutting, scraping or abrading surface, or blade. Although the "cutting" surfaces or blades of an interventional catheter of the present invention may be sharp and may actually "cut" material at the target site, the term "cut" or "cutting" or "cutter" or "blade(s)," as used herein, refers to cutting, scraping, abrading, ablating, macerating and otherwise breaking down undesired material into particles or smaller, removable, units of material.

In some embodiments, interventional catheters incorporate cutter assemblies comprising a plurality of cutting blades. Such cutter assemblies may incorporate fixed and/or adjustable blades. Suitable cutter assemblies are disclosed, for example, in U.S. Pat. Nos. 6,565,588 and 6,818,001, which are incorporated herein by reference in their entireties. Suitable differential cutting blades are also disclosed, for example, in U.S. Patent Publication 2004/0006358 A1, which is incorporated herein by reference in its entirety. In some embodiments, the operating head may comprise an abrasive surface or an abrasive material provided on a surface of a rotational element. Interventional catheter operating heads comprising abrasive materials are well known in the art. In another embodiment, the operating head comprises at least one blade or cutter element positioned and oriented to exit a window, separate material from an inner lumen wall, and collect the material in an internal space. In an alternative embodiment, the operating head may comprise another type of ablating device, such as a plaque excision device, a laser ablation or high frequency ultrasound ablation device, or a radio frequency, heat-producing or electrical device that operates to remove unwanted material from body lumens or cavities.

The drive shaft that conveys rotation and torque from a drive system to the operating head must be small enough and flexible enough to be navigated through small and tortuous passageways during navigation of the operating head to the target removal site, and must have sufficient mechanical integrity to transfer high rotational and torque loads, and operate in a high vacuum, or aspirate withdrawal, environment. Multi-filar helical coils are used as drive shafts in many types of interventional catheters having a rotatable operating head. Suitable drive shafts are well known in the art and are described in the patent publications incorporated herein by reference.

Interventional catheters disclosed herein preferably incorporate an aspiration system for removal of debris from the intervention site via aspiration through one or more aspiration ports. Aspiration systems suitable for use in interventional catheters of the present invention are described, for example, in the patents incorporated herein by reference and in U.S. Patent Publication 2004/0220519 A1, which is also incorporated herein by reference in its entirety. Debris generated during a material removal operation is entrained in fluids (e.g. blood), and the aspirate fluid containing debris is removed by aspiration through the material removal port(s) and withdrawn through a sealed lumen of the interventional catheter. The sealed lumen is connectable to a vacuum source and aspirate collection system.

In one embodiment of interventional catheters of the present invention, at least one aspiration port having a generally large opening is provided in proximity to the operating head (e.g., the cutter or plaque excision assembly). The aspiration port may be provided directly in a catheter structure, or it may be provided in a rigid shell structure mounted directly or indirectly to a distal portion of the catheter. Debris generated during a material removal operation is entrained in fluids (e.g. blood and infusate), and the aspirate fluid containing debris is removed by aspiration through the material removal port(s) and withdrawn through a sealed lumen of the interventional catheter. The sealed lumen is connectable to an aspirate conduit and aspirate collection system. In some embodiments, at least one large aspiration port is positioned proximal to the operating head. Generally smaller material aspiration ports may additionally be disposed on one or more surfaces of the cutter assembly itself.

The interventional catheter may additionally incorporate a masticator assembly positioned for rotation inside the aspiration port to facilitate removal and breaking down of debris withdrawn from the site of intervention through the port. The rotatable masticator assembly may comprise a central core structure having one or more projecting bars, extending generally along the length of the central core. The central core structure is rotated during operation of the operating head. When the operating head comprises a rotating structure, the masticator assembly may be directly or indirectly connected to the same drive system that rotates the operating head.

The exposed outer surfaces of the projecting bars provided on the masticator central core structure are generally curved and, in some embodiments, generally match the curved profile of the inner surface of a shell structure in which the aspiration port is provided. The projecting bars may have a tapered structure, with a narrower profile toward a proximal end of the masticator assembly and a wider profile toward a distal end of the masticator assembly. The bars may also be configured so that their side walls have different dimensions and different undercut angles along the length of the bars. In general, the side walls are higher and have a smaller undercut angle toward a proximal end of the masticator assembly and are lower and have a larger undercut angle toward a distal end of the masticator assembly. As particulate material is drawn into the aspiration port by aspiration forces, the rotating macerator assembly facilitates further breakdown of the material and assists in moving the particulate material proximally and through the aspiration conduit for downstream collection and disposal.

Liquid infusion may be provided in, or in proximity to, the operating head. Infusion of liquids may be used to provide additional liquid volume for removal of debris, or to deliver lubricating fluids, diagnostic or treatment agents, contrast agents and the like. Infusion of fluids such as saline in proximity to the target material removal area may be desirable because it tends to reduce the viscosity of the materials being removed, thus facilitating removal through relatively small diameter lumens. Infusion of liquids also desirably tends to reduce the volume of blood removed during a material removal operation, thereby reducing blood loss and allowing longer procedures if necessary. In addition, infusion of liquids reduces vessel collapse and keeps the vessel wall in tension, thereby improving the effectiveness of cutting and reducing damage to the vessel wall. Liquid infusion may also reduce guidewire friction in embodiments where guidewires are employed. Many different types of infusion systems are known and may be used in interventional catheters of the present invention.

In certain embodiments, the interventional catheter disclosed herein is provided with an elongated, generally cylindrical liner or bushing that extends through the guidewire lumen at a distal portion of the operating head and, optionally, through a substantial portion of the operating head. In some embodiments, the guidewire lumen bushing may extend from a distal portion of the operating head through the operating head and into a distal portion of the catheter. In one embodiment, the liner is provided with an enlarged diameter distal region in proximity to the operating head.

The use of a guidewire lumen bushing in proximity to the distal portion of the operating head contributes to reducing the amount of blood, thrombus and/or debris that enters the guidewire lumen through the guidewire exit port during aspiration and may also contribute to maintenance of generally high and consistent aspiration pressure, thereby providing improved and more consistent removal of debris and fluids from the site during operation of the operating head and aspiration system.

BRIEF DESCRIPTION OF THE DRAWINGS

FIG. 7 illustrates an enlarged cross-sectional view of the aspiration assembly of FIG. 5 taken through line 7-7.

FIG. 8 illustrates an enlarged cross-sectional view of the aspiration assembly of FIG. 5 taken through line 8-8.

FIG. 9 illustrates an enlarged cross-sectional view of the aspiration assembly of FIG. 5 taken through line 9-9.

FIG. 10A illustrates a distal portion of an interventional catheter assembly of the present invention, FIG. 10B provides a further enlarged illustration of the distal portion of the interventional catheter assembly shown in FIG. 10A distal to line 10B of FIG. 10A, FIG. 10C provides a further enlarged illustration of the interventional catheter assembly shown in FIG. 10A between the lines 10C shown on FIG. 10A, and FIG. 10D shows an enlarged illustration of another embodiment of a distal portion of an interventional catheter assembly of the present invention.

DETAILED DESCRIPTION

Certain preferred embodiments are described herein with reference to a material removal device having a rotational cutting head. It will be appreciated that this device embodiment is being described as illustrative and that the inventions and features disclosed herein are applicable to interventional catheters having different types of operating heads.

Figure 1:
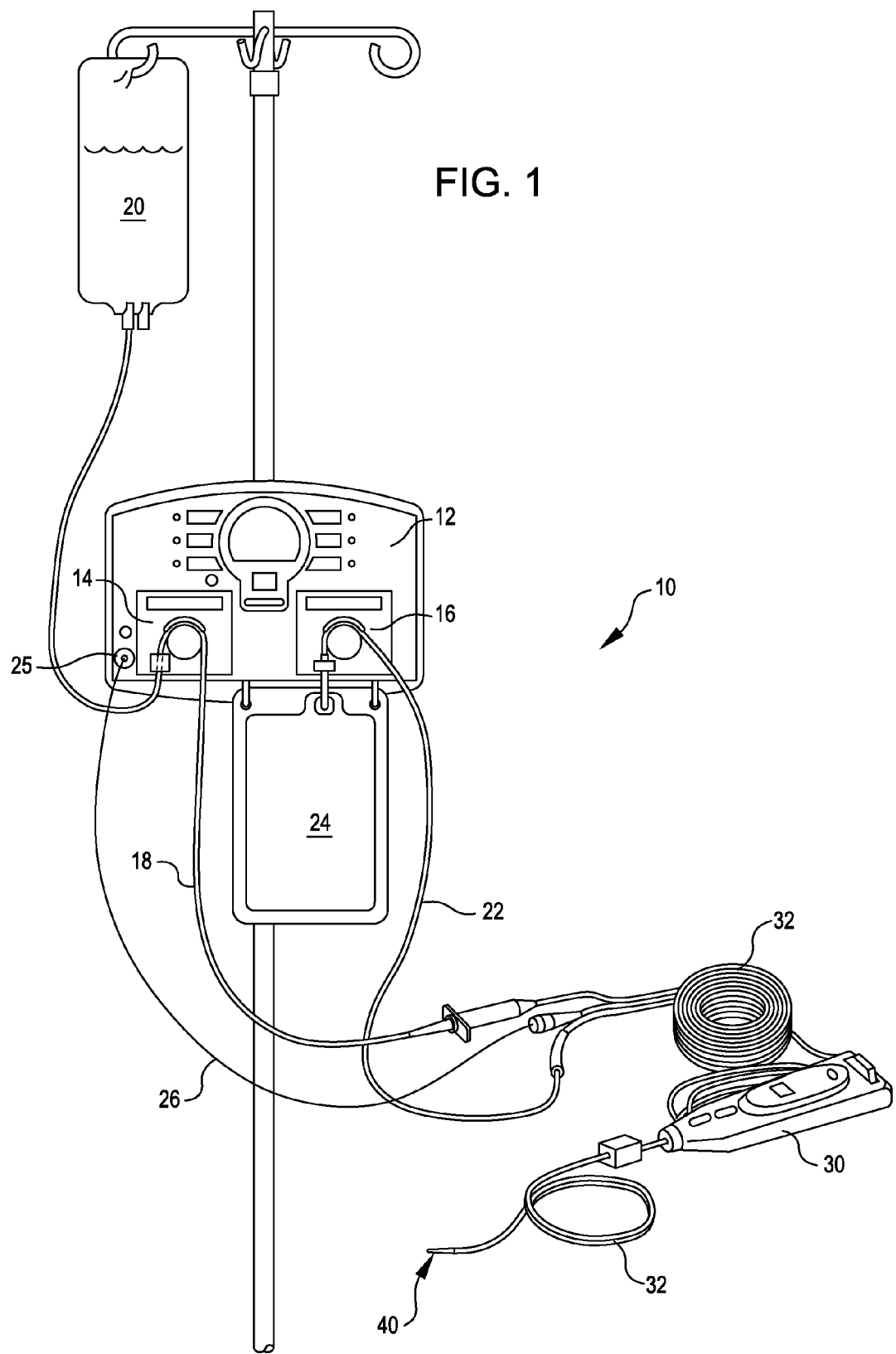
FIG. 1 is a schematic diagram of an interventional catheter assembly comprising an operating head mounted at or near a distal end of a catheter system, a controller and a console unit.

FIG. 1 illustrates an exemplary embodiment of an interventional catheter assembly, including a console unit incorporating aspiration and infusion systems as disclosed herein. Interventional catheter assembly 10 comprises console unit 12, controller 30, and catheter system 32 having an operating head 40 located at or in proximity to the distal end of the catheter system. Controller 30 may be used to manipulate (e.g. advance and/or rotate) the catheter system 32 and operating head 40, or alternative controls may be provided.

Console unit 12 incorporates an infusion pump 14 and an aspiration pump 16. During operation of the interventional catheter, an infusate conduit 18 draws fluid from an infusate reservoir 20 and operably contacts the infusion pump 14 to provide fluid flow through an infusion lumen in catheter system 32 to one or more infusion ports provided in proximity to the operating head 40. Similarly but in reverse, fluids with entrained particulates are withdrawn from the site of intervention through an aspiration lumen in catheter system 32 and conveyed to aspiration conduit 22, which is in operable contact with the aspiration pump 16, and communicates with the aspirate collection vessel 24. Console unit 12 may also provide a power source for operating the operating head and system components, or it may be in communication with an external power source. In the illustrated embodiment, console unit 12 provides power to the interventional catheter assembly and controller 30 by means of a device power port 25 and power cord 26.

Various microprocessor, electronic components, software and firmware components may be provided within or in communication with the console unit for controlling operation of the interventional catheter as described herein. Software may be provided in a machine-readable medium storing executable code and/or other data to provide one or a combination of mechanisms to process user-specific data. Alternatively, various systems and components may be controlled using hardware or firmware implementations. Data storage and processing systems may also be provided in console unit 12.

One function of console unit 12 is to provide feedback of system and/or environmental conditions or operating parameters. The console unit may output operational information concerning operating conditions and feedback from the material removal site to the operator. According to one embodiment, console unit 12 provides continuously updated output to an operator of operating parameters such as operating head rotation rate, which may include the actual run speed as well as the desired speed; operating head advance rate; aspiration rate and/or volume; infusion rate and/or volume; elapsed run time; and the like.

Certain automated and selectable control features may be implemented in console unit 12. Preset routines or programs involving various operating parameters may be preselected, stored and selectable by an operator, for example. Thus, according to one embodiment, the disclosed material removal system implements control features based on an operator's input of specified parameters. Specified parameters may include, for example: lesion length, lesion type and character, such as calcified, fibrotic, lipid/fatty and the like; historical factors, such as restenosis; rate of blood flow; volume of blood flow; percentage of restriction; lumen type and/or location; lumen diameter; desired rotation rate and/or rotation profile for the cutter assembly; desired advance rate and/or advance profile for the cutter assembly; desired aspiration rate and/or profile; desired infusion rate and/or profile; and the like. Based on the specified parameters input by the operator, the control unit may calculate and implement automated operating conditions, such as cutter assembly rotation rate and profile; cutter assembly advance rate and profile; aspiration rate and profile; infusion rate and profile; cutter assembly size; and the like. Various system operating parameters, operating conditions, patient conditions, and the like may also be recorded and stored during interventions to preserve a record of the patient and intervention operational parameters.

High efficiency aspiration is important in the interventional catheter systems disclosed herein. In certain embodiments, fluid and associated particulates are aspirated from the intervention site at rates of at least 15 ml/min of operating head run time and in many embodiments, fluid and associated particulates are aspirated at rates of at least 25 ml/min of operating head run-time. In exemplary interventional catheter systems, the aspiration site may be more than a meter away from the controller 30 through an aspirate removal passageway located within the catheter system 32 and having a diameter of less than 0.10 inch, for example between about 0.050 to 0.070 inch. The distance that the aspirate travels between controller 30 and console unit 12 may be from about 0.5 meter to several meters, through an aspirate conduit that is between about 0.125 inch to about 1.0 inch in diameter. The blood and debris being aspirated are relatively viscous fluids, and achieving a relatively constant and high level of aspiration under these conditions is essential.

In one embodiment, aspiration pump 16 comprises a multi-lobed roller pump. The rotation rates of multiple rollers, or of a multi-lobed rotating structure, may be variable or selectable to control the aspiration rate and volume. Roller pumps permit fluid to flow in a conduit through the rollers of the pump at atmospheric pressure, and thus reduce or prevent the formation of bubbles and foam in the liquid being evacuated. Because the aspirate is at atmospheric pressure when it exits the roller pump, a simplified, atmospheric pressure collection vessel may be used rather than an evacuated collection vessel. A simple bag or another collection vessel, such as those used for collection of blood, may be used. For example, a collection bag 24 and a sealed aspiration conduit may be provided as part of a sterile disposable interventional catheter kit. A distal end of the aspiration conduit may be pre-mounted on and sealed to the controller 30. A proximal portion of the aspiration conduit is mounted on the aspiration pump 16 prior to operation of the interventional catheter and the aspirate collection bag is mounted to or in proximity to the control module 12.

Infusion pump 14 may also comprise a multi-lobed roller pump employing variable or selectable rotation rates to control the infusion rate and volume. A simple bag or another infusate reservoir, such as those used for intravenous infusions, may be used to supply the infusate. For example, an infusate reservoir 20 having a sealed conduit that is mounted in the infusion pump 16 during operation of the interventional catheter may be provided. In this embodiment, the sealed infusate conduit may be provided as part of the sterile disposable interventional catheter system and a distal end of the aspiration conduit may be pre-mounted on and sealed to the controller 30. A proximal portion of the infusate conduit may be connected to an infusate reservoir 20, such as a saline bag, and mounted in proximity to the infusion pump 14 prior to operation.

In one embodiment, console unit 12, together with aspiration pump 16 and infusion pump 14 and the associated control and display features, is provided as a separate, re-usable unit, that may be used as standard equipment in operating rooms, for example. In the system illustrated, console unit 12 is not contaminated by contact with blood or aspirate during operation, and the power and control systems are durable and long-lasting and may be reused for many interventions. Console unit 12 may be provided in a housing designed to sit on a platform during operation, or the housing may be designed for mounting on a portable structure, such as an i.v. pole or another structure. The interventional catheter system, comprising the catheter system 32 with operating head 40, the controller 30, aspirate conduit 22, aspirate collection vessel 24, and infusion conduit 18 may be provided as a sterile, single use system kit.

The catheter system and operating head are described below with reference to a rotatable operating head employing a cutting material removal mechanism. In this application, aspiration and infusion conduits terminate at or within controller 30, where they communicate with aspiration and infusion lumens within the catheter system 32. A rotatable drive shaft for driving the operating head is provided in catheter system 32. A guidewire may also transit controller 30 and catheter system 32. In general, controller 30 or an associated control mechanism provides user-operated mechanisms for rotating and/or translating the operating head. Controller 30, which is constructed from a durable, sterilizable material, such as hard plastic, may be provided in any convenient ergonomic design and constructed for placement in proximity to and/or in contact with the external body. In one embodiment, the controller may include an integrated handle for operator convenience in holding and supporting the controller during operation. Catheter system 32, exiting controller 30, is axially translatable with respect to controller 30 as the operating head and catheter system are guided to a target material removal site. It will be appreciated that some of the control and operational features described herein with reference to controller 30 may be provided in console unit 12 and, likewise, some of the control and operational features described with reference to console unit 12 may be provided in controller 30.

The operating head 40 of the interventional catheter disclosed herein may comprise any of a variety of rotational cutting devices or assemblies having one or more cutting surface(s) for cutting, fragmentizing, pulverizing, ablating, scraping, grinding or otherwise reducing the size of undesired material and/or separating undesired material from healthy tissue, such as the walls of a blood vessel, in proximity to the target removal site. Differential cutter assemblies may be provided, as described in the U.S. patent publications incorporated herein by reference. Operating heads comprising abrasive rotational surfaces may also be used. The operating head, or sub-components thereof, such as the cutting surfaces, may be coated with a radio-opaque material such as gold, platinum, inks and the like, to render the operating head radioscopically visible and to assist a medical professional in guiding and positioning the cutter assembly relative to an occlusion. In certain embodiments of interventional catheters of the present invention, non-rotational operating heads may also be used that incorporate alternative material removal modalities, such as laser or ultrasound ablation techniques, or other types of ablation techniques.

Figure 2:
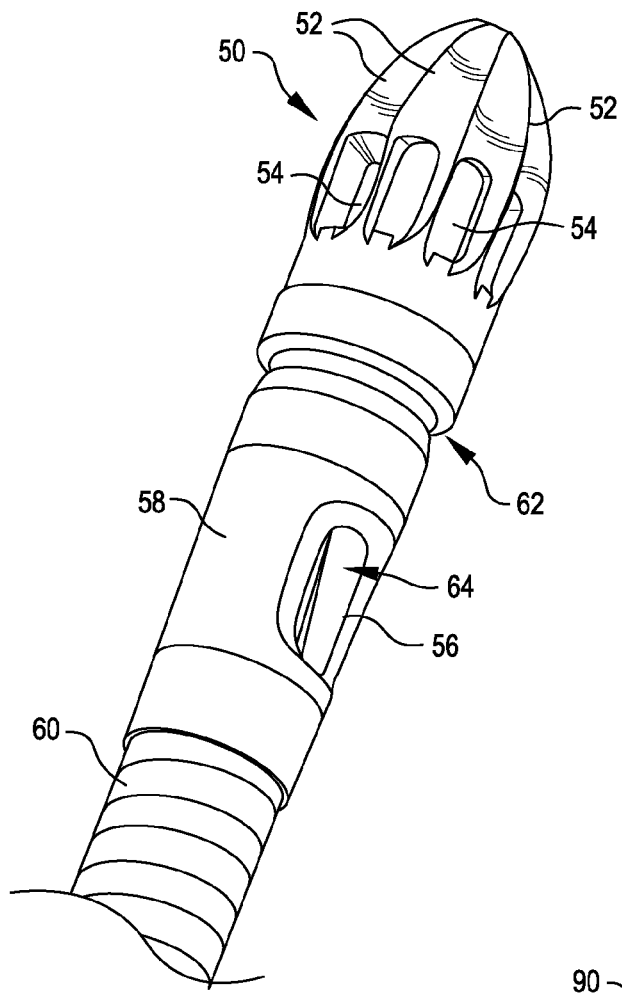
FIG. 2 illustrates an enlarged perspective view of an interventional catheter of the present invention having a distal operating head with ports for aspiration or infusion and a proximal tubular structure having a relatively large port for aspiration.

FIG. 2 illustrates the distal end of one embodiment of an interventional catheter of the present invention. In this embodiment, the operating head comprises a multi-bladed cutter assembly 50 having a plurality of raised blades 52 arranged in a radially symmetrical configuration. Blades 52 are preferably differential cutting blades, and cutting assembly 50 may incorporate a plurality of ports 54 arranged in a radially symmetrical configuration in the spaces between blades 52. Ports 54 are shown provided between each set of neighboring blade structures in FIG. 2, but it will be appreciated that fewer ports may be provided. Ports 54 are preferably provided in a generally proximal portion of cutter assembly 50 and may have a generally oblong configuration, as illustrated, or may take a variety of other configurations.

The distal end of the interventional catheter illustrated in FIG. 2 additionally comprises a large port 56 located in a distal portion of the catheter, or a proximal portion of the cutter assembly, proximal to blades 52. Port 56 is generally provided as a window or cut-out in a cylindrical structure and preferably spans at least 10% of the circumference of the structure; more preferably at least 20% of the circumference of the structure; and yet more preferably at least 30% of the circumference of the structure. The cylindrical structure supporting port 56 may be a distal catheter portion, or port 56 may be provided in a generally cylindrical tubular shell structure mounted, directly or indirectly, to a distal catheter portion 60. In one embodiment, illustrated in FIG. 2, a rigid cylindrical shell 58 is mounted to distal catheter portion 60 at its proximal end and is mounted to, or forms a stationary element of, bearing 62 at its distal end. Bearing 62 allows distal catheter portion 60 and cylindrical shell 58 to remain stationary during rotation of cutting assembly 50. Bearing 62 may also provide limited articulation of cutting assembly 50 about its longitudinal axis.

In the embodiment illustrated in FIG. 2, ports 54 may be operated as aspiration or infusion ports and enlarged proximal port 56 operates as an aspiration port and incorporates a rotating macerator assembly 64, which is described in greater detail below. In one embodiment, proximal port 56 is provided as an aspiration port and communicates with an aspiration lumen within catheter 60 that communicates with aspiration conduit 22, while ports 54 operate as infusion ports and communicate with an infusion lumen within catheter 60 that communicates with infusion conduit 26.

Figure 3:
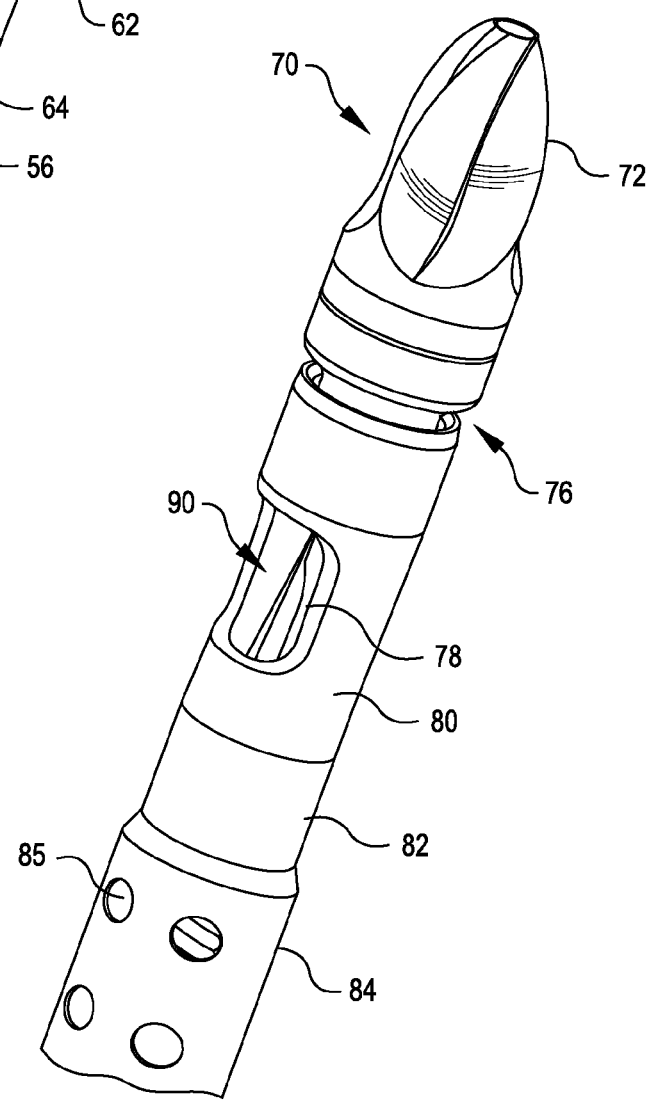
FIG. 3 illustrates an enlarged perspective view of an interventional catheter of the present invention having a distal operating head, a proximal aspiration port and liquid infusion ports located proximally to the aspiration port.

In another embodiment of an interventional catheter of the present invention illustrated in FIG. 3, operating head 70 comprises a distal cutter assembly 72 mounted to a bearing system 76 that allows rotation of the operating head while the catheter components proximal to the operating head remain stationary during rotation. The interventional catheter illustrated in FIG. 3 additionally comprises a proximal aspiration port 78 provided as an opening in a cylindrical shell structure 80 located proximal to the cutter assembly 72. Aspiration port 78 communicates with an aspiration lumen within catheter 82 that communicates proximally with aspiration conduit 22.

Proximal aspiration port 78 may be provided as an opening or window in a distal catheter portion, or it may be provided as an opening in a substantially rigid cylindrical shell 80, as illustrated. Cylindrical shell 80 is constructed from a generally rigid, durable material, such as surgical steel or stainless steel, and has a length that is approximately the same as that of the cutter assembly. Shell 80 is generally mounted to, or forms a stationary component of, bearing 76 at its distal end. Bearing 76 allows catheter 82 and cylindrical casing 80 to remain stationary during rotation of operating head 50. Bearing 76 may also provide limited articulation of operating head 70 about its longitudinal axis.

Aspiration port 78 may be provided as a window spanning at least 10% of the circumference of the shell structure; more preferably at least 15% of the circumference of the shell structure; more preferably at least 25% of the circumference of the shell structure; and yet more preferably at least 35% of the circumference of the shell structure. The proximal aspiration port may be provided, for example, in a generally ovoid, rectangular, or square profile. The surface area, or size of the opening of port 78 depends on the relative sizes of the operating head, the catheter and the size of debris that is anticipated will be generated during operation of the operating head. In one embodiment, port 78 has a length in the direction of the longitudinal axis of the interventional catheter that is from about 0.5 to about 2.5 times the transverse width of the port as measured on the arc of the cylindrical surface, preferably from about 0.7 to about 2.0 times the transverse width of the port. In certain embodiments, aspiration port 78 has an opening, or surface area that is between about 0.3 to about 20 mm$^2$, preferably between about 0.5 and 10 mm$^2$ in surface area.

The interventional catheter of FIG. 3 incorporates a macerator assembly 90 mounted for rotation inside cylindrical shell 80. Macerator assembly 90 rotates within the inner cavity of cylindrical shell 80 and has projecting bars, described in detail below, that interact with walls of the aspiration port 78 and the inner surface of cylindrical shell 80 to grind or macerate debris that is aspirated through port 78.

The interventional catheter illustrated in FIG. 3 additionally incorporates a plurality of infusion ports 85 located proximally with respect to aspiration port 78, but in proximity to the aspiration port and operating head 70. Infusion ports 85, which may be provided in an outer sheath 84, as shown in FIG. 3, communicate with an infusion lumen in the catheter assembly, which communicates with infusion conduit 26. In certain embodiments, between two and twenty, for example twelve, infusion ports 85 are provided in an infusion sheath 84 mounted to distal catheter 82. The infusion ports may have a generally uniform size, or infusion ports of different sizes may be provided. The infusion ports may be generally cylindrical, as shown in FIG. 3, or they may have alternative configurations. Each infusion port 85 may have a diameter of approximately 0.005 in. to 0.20 in., more preferably from about 0.006 in. to about 0.015 in. Infusion ports having diameters of about 0.010 in. are especially preferred for certain applications. In one embodiment, the infusion ports are spaced in a generally circumferential pattern to provide a substantially uniform flow of infusate around the circumference of the infusion sheath.

Figure 4:
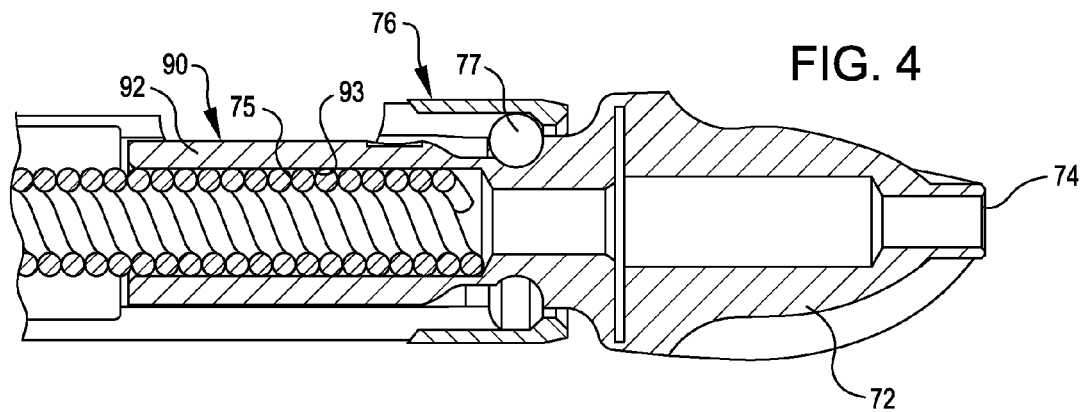
FIG. 4 illustrates an enlarged cross-sectional view of an interventional catheter of the present invention having a distal operating head and a proximal aspiration port with an internal rotating member.

FIG. 4 shows a cross-sectional view of the distal end of the interventional catheter illustrated in FIG. 3. Distal cutter assembly 72 has an internal guidewire lumen terminating in guidewire exit port 74. This view illustrates a helical rotational drive 75, which is mounted inside a central cavity in the core structure of macerator assembly 90 and fixed to the macerator, providing rotation of macerator assembly 90. In embodiments employing a rotating operating head, drive 75 additionally drives the operating head, directly or indirectly. A bearing 76 member comprising a plurality of ball bearings 77 may be provided between the rotating cutter assembly 72 and/or the rotational macerator assembly 90 and the static cylindrical casing 80 and catheter 82.

Figure 5:
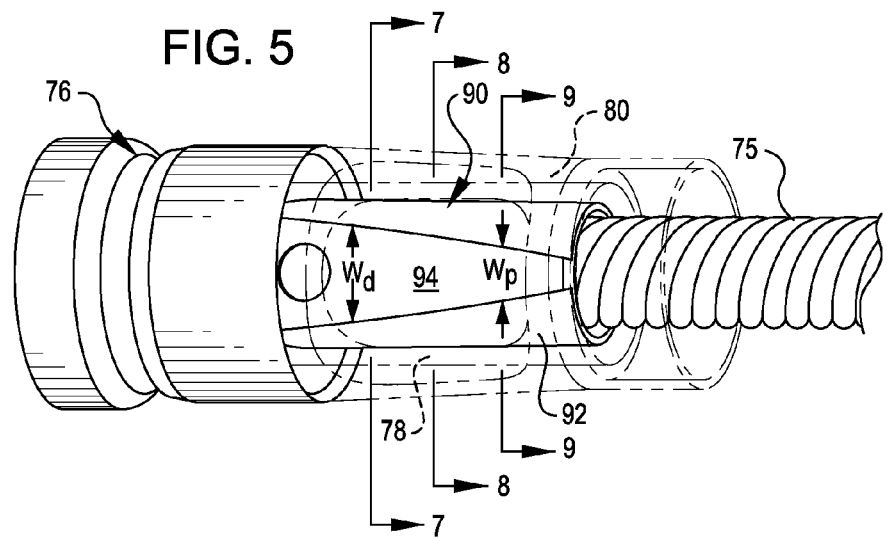
FIG. 5 illustrates an enlarged view of an aspiration window and internal rotating macerator element of the present invention.
Figure 6:
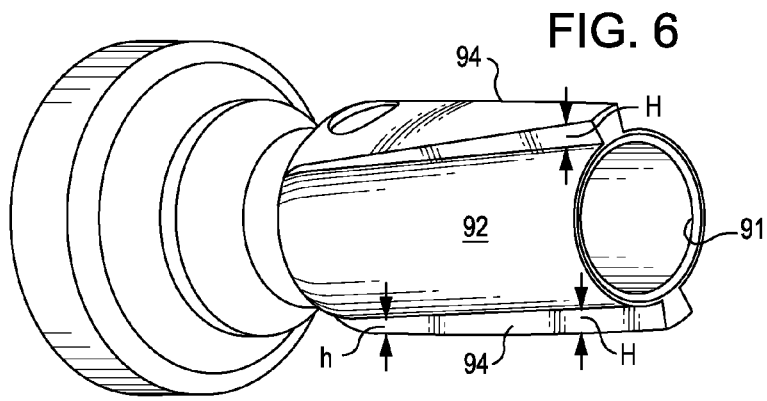
FIG. 6 illustrates an enlarged perspective view of the internal rotating macerator element.

The rotating macerator 90, as illustrated in FIGS. 5 and 6, comprises a central core structure 92 and at least one projecting bar 94 aligned generally with the longitudinal axis of the interventional catheter. The central core structure 92 preferably has a generally cylindrical internal bore 91. Multiple projecting bars 94 may be provided and are preferably arranged in a radially symmetrical arrangement with respect to the longitudinal axis of the catheter assembly. In one embodiment, illustrated in FIGS. 6-9, two projecting bars are provided.

Projecting bars 94 preferably have a curved exterior surface that generally matches and rotates freely in the interior surface of cylindrical casing 80. In the embodiment illustrated in FIGS. 5 and 6, the width W of the arced exterior surface of the upstanding bars 94 tapers from a distal end ($W_d$) to a proximal end ($W_p$) of the rotating macerator. The proximal portion of projecting bar 94 has a narrower profile $W_p$ that may be from about 5% to about 75% the width of the distal end profile $W_d$. In one embodiment, the external diameter of central core structure 92 tapers from a larger diameter at the distal end to a smaller diameter at the proximal end. Consequently, upstanding bars 94, as illustrated, may have a higher profile with respect to the surface of the central core structure 92 at the proximal end than at the distal end. In some embodiments, the radial height H of projecting bars 94 at a proximal portion measured from the surface of central core structure 92 is preferably at least about 50% greater than the radial height h of projecting bars 94 at a distal portion of the macerator assembly measured from the surface of central core structure 92. In some embodiments, the radial height H of projecting bars 94 at a proximal portion measured from the surface of central core structure 92 is preferably at least about 100% greater than the radial height h of projecting bars 94 at a distal portion of the macerator assembly.

FIGS. 7-9 illustrate exemplary geometries of the macerator element and upstanding bars at various points along the macerator assembly 90, with FIG. 7 illustrating a cross-sectional view at a generally distal end of the macerator assembly, FIG. 8 illustrating a cross-sectional view at a generally central portion of the macerator element, and FIG. 9 illustrating a cross-sectional view at a generally proximal end of the macerator element. A multi-filar drive 75 and a central guidewire lumen 86 are visible. Window 78 is shown as a cut-out section of cylindrical casing 80 having a generally blunt perimeter wall 79. The outer walls 93 of projecting bars 94 are illustrated having an arced surface that generally matches the internal surface of cylindrical casing 80 so that macerator assembly 90 is freely rotatable within cylindrical casing 80 about the longitudinal axis of the interventional catheter. The change in width of upstanding bars 94 from a wider distal end illustrated in FIG. 7 to a narrower proximal end illustrated in FIG. 9 is also evident.

Angled walls 95 are provided between the outer walls 93 of projecting bars 94 and the exterior surface of central core structure 92. Angled walls 95 are generally configured to present an undercut angle of from about 10° to about 60° with respect to a line bisecting the upstanding bar and intersecting the central longitudinal axis of the macerator assembly. The undercut angles of angled walls 95 may be from about 20° to about 45° in certain embodiments. The undercut angle of walls 95 is preferably greater at the distal end of the macerator assembly, as illustrated in FIG. 7, and less at the proximal end of the macerator assembly. In the embodiment illustrated, the undercut angle is 39° at a distal portion of the macerator device (FIG. 7); 32° at a central portion of the macerator device (FIGS. 8) and 24° at a proximal portion of the macerator device. The difference in undercut angle between a distal end and a proximal end of the macerator assembly is preferably at least about 10°, more preferably at least about 15° and, in some embodiments, up to about 20° or 30°.

The angle formed between the undercut angle of walls 95 of the projecting bar(s) and the face 79 of window 78 may also be adjusted to facilitate breaking down of particulates. In some embodiments, as illustrated in FIG. 8, the angle formed by the undercut angle of the projecting bar wall and the face of the aspiration window is about 32°. This angle also changes with changes in the undercut angles of the projecting bars and may range from about 15° to about 60° from the distal to the proximal end of the macerator assembly, more preferably from about 20° to about 50°.

During operation of the cutter assembly or operating head, the central core and upstanding bars of macerator assembly 90 rotate, while the aspiration port and cylindrical shell structure in which the aspiration port is provided remain static. As the upstanding bars rotate and debris is aspirated through the aspiration window, the upstanding bars interact with the wall of the aspiration port and the interior surface of the cylindrical structure to shear, grind, macerate and/or break-up debris as it enters the aspiration port and is aspirated through the aspiration lumen. The tapered structure and undercut walls of the upstanding bars also facilitate movement of fluid and debris proximally in the macerator assembly to the aspiration lumen. The rotating element of the macerator assembly does not extend radially beyond the inner wall of the cylindrical structure and aspiration port, and is generally constructed from a rigid material such as, but not limited to, hardened stainless steel, titanium or titanium nitrate-coated stainless steel.

Figure 10A:
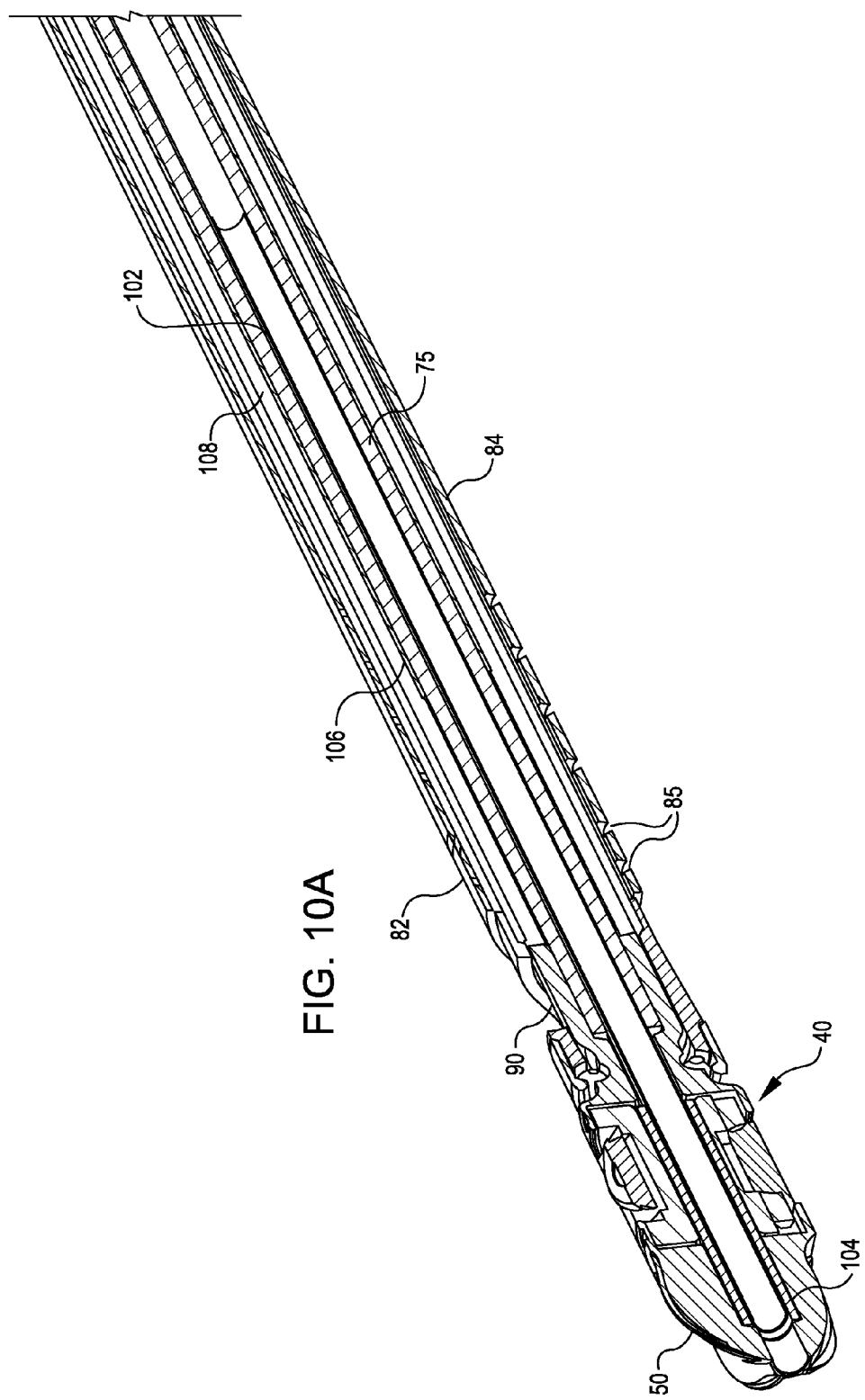
FIGS. 10A-D illustrate enlarged cut-away cross-sectional views taken along a central longitudinal plane of additional embodiments of an interventional catheter assembly of the present invention having a liner or bushing positioned within a guidewire lumen.
Figure 10B:
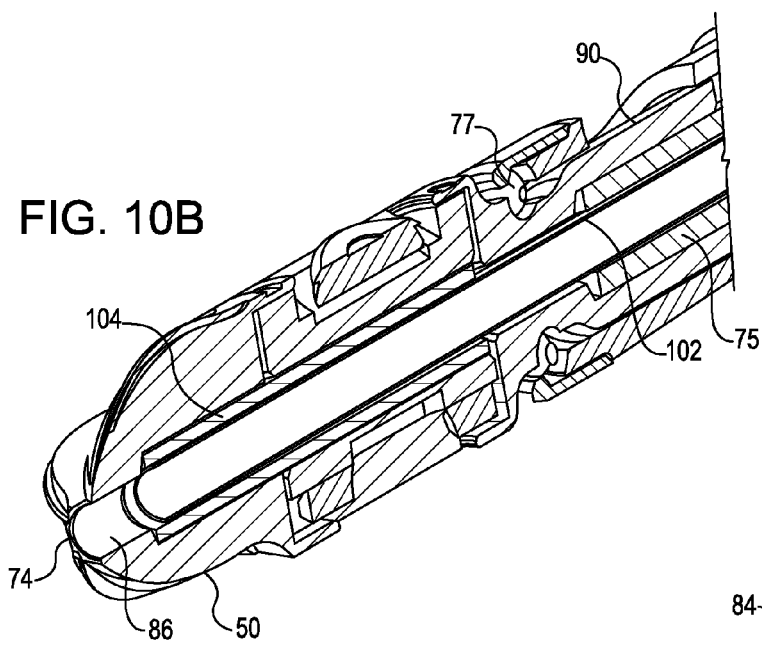
Figure 10C:
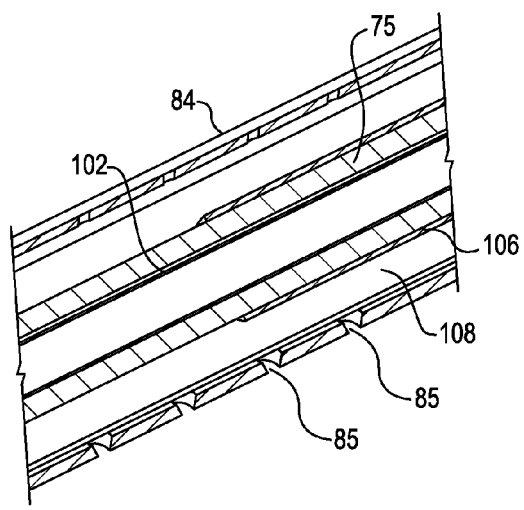

FIGS. 10A-C illustrate an embodiment of an interventional catheter system 100 in which an elongated cylindrical liner, or guidewire lumen bushing 102, extends from a distal region of the operating head proximally through the operating head and into a distal region of the catheter 82. Bushing 102 effectively provides a lining structure and internal surface along the wall of the guidewire lumen in proximity to the distal guidewire port. Introduction of guidewire lumen bushing 102 reduces the effective diameter, and volume, of the guidewire lumen, thereby reducing the clearance between the guidewire and the internal surface of the guidewire lumen. This reduced clearance restricts entry of blood, thrombus and/or other debris into guidewire lumen 86. Providing reduced clearance between the guidewire and the internal surface of the guidewire lumen in proximity to the distal guidewire port also desirably promotes maintenance of consistent and generally high aspiration pressures and volumes during operation of the interventional catheter and aspiration system. In some embodiments, the bushing is dimensioned to provide clearance of less than about 0.005" between the internal bushing surface and a recommended guidewire surface; in other embodiments, the bushing is dimensioned to provide clearance of less than about 0.003" between the internal bushing surface and a recommended guidewire surface; in yet other embodiments, the bushing is dimensioned to provide clearance of between about 0.0015" and 0.0005" between the internal bushing surface and a recommended guidewire surface.

Figure 10D:
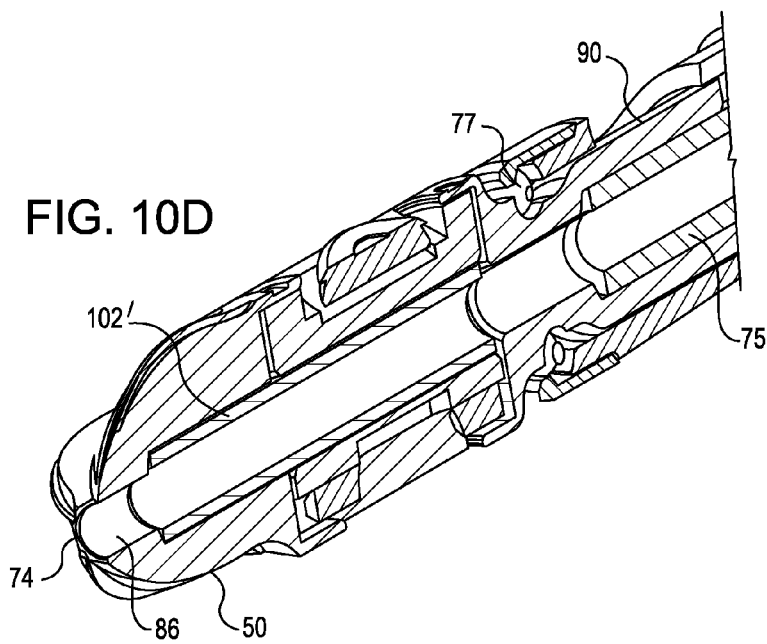

In the embodiment illustrated in FIGS. 10A-10C, guidewire lumen bushing 102 extends longitudinally through internal guidewire lumen 86 from a region just proximal to guidewire exit port 74 in operating head 40, through macerator assembly 90 to a region proximal to infusion ports 85, and terminates proximally of the distal region of aspiration lumen 108. In this embodiment, bushing 102 extends through the internal guidewire lumen in both the operating head and a distal portion of the catheter. In alternative embodiments, as shown in FIG. 10D, a bushing 102' providing reduced clearance between the guidewire and the internal surface of the guidewire lumen may be provided in the operating head alone without extending proximally into a distal portion of the catheter.

Guidewire lumen bushing 102 is preferably made from a durable, chemically resistant and fluid impermeable material such as polyimide. The rigidity or flexibility of the bushing may be determined, as desired, by using selected materials and/or by providing bushings having different wall thicknesses. In the embodiment shown in FIGS. 10A and 10B, bushing 102 has regions having different dimensions along its length, with a distal region 104 that traverses the operating head having an enlarged outer diameter compared to a proximal region of the bushing. Bushing 102 may thus have a larger outer diameter distal region and a smaller outer diameter proximal region. The inner diameter of guidewire lumen bushing 102 may be constant along its length, or the inner diameter may vary in different regions.

In one embodiment, enlarged outer diameter distal region 104 of guidewire lumen bushing 102 is formed by providing a larger diameter tube overlying the outer surface of the distal portion of a tubular structure forming bushing 102. For example, enlarged distal region 104 can be formed by bonding a second, shorter section of larger diameter polyimide tube to an underlying polyimide tube forming the proximal region of bushing 102 using a bonding agent such as cyanoacrylate. Alternatively, enlarged distal region 104 can be provided by using a stepped down tube as bushing 102. In yet another embodiment, two tubes having different outer diameters and dimensions may be interfaced at an interface region by proximity and/or bonding to form an integral bushing.

In one embodiment, guidewire lumen bushing 102 has a length sufficient to extend from a region in proximity to a distal guidewire exit port through a substantial portion of an operating head. In another embodiment, bushing 102 has a length sufficient to extend from a region in proximity to a distal guidewire exit port to a region proximal to one or more aspiration port(s), and, in some embodiments, the bushing extends to a region proximal to all aspiration port(s). In yet another embodiment, bushing 102 has a length sufficient to extend from a region in proximity to a distal guidewire exit port to a region proximal to one or more infusion port(s), and, in some embodiments, the bushing extends to a region proximal to all infusion port(s).

In the embodiment illustrated in FIGS. 10A-10C, operating head 40 is operably connected to a drive shaft 75 that, during operation of the interventional catheter, rotates the operating head at a high rate of rotation. Drive shaft 75 may extend to, or distally from, macerator assembly 90 and an associated aspiration port; drive shaft 75 may also extend to, or distally from, one or all aspiration port(s) and one or all infusion port(s). An aspiration lumen 108 may be provided between the outer surface of drive shaft 75 and an inner surface of catheter 82 or an associated catheter or sheath structure for active removal of fluids and debris during operation of the interventional catheter. A liner or sheath 106 may be provided overlying an outer surface of the drive shaft 75, the distal termination of sheath 106 being proximal to the operating head. In preferred embodiments, guidewire lumen bushing 102 extends to a location proximal to the distal termination of drive shaft sheath 106. In the embodiment illustrated in FIG. 10D, the same operating head and interventional catheter components may be implemented, with a guidewire lumen bushing 102' provided in the operating head alone, without extending proximally into a distal portion of the catheter.

In one embodiment, the guidewire lumen bushing has a length of less than about 2 in., with a length of about 1 in. being preferred for many embodiments. The guidewire lumen bushing may have an internal diameter of less than about 0.025 in., with an internal diameter of about 0.015 in. being preferred for many embodiments. In one embodiment, the outside diameter of distal region 104 of the guidewire lumen bushing is at least about 0.040 in., with an outer diameter of about 0.026 in. being preferred for many embodiments. The outside diameter of the proximal region of guidewire lumen bushing 102 may be at least about 0.025", with a proximal region outer diameter of about 0.017 in. being preferred for many embodiments.

The present invention has been described with reference to specific embodiments and figures. These specific embodiments should not be construed as limitations on the scope of the invention, but merely as illustrations of exemplary embodiments. It is further understood that many modifications, additions and substitutions may be made to the described interventional catheter and control system without departing from the scope of the present invention.

We claim:

1. An interventional catheter assembly comprising:
   (a) an elongated tubular catheter for navigation within a patient's body;
   (b) an operating head mounted at a distal end of the catheter;
   (c) a guidewire lumen extending through the catheter and the operating head;
   (d) at least one aspiration port in proximity to the operating head in communication with an aspiration lumen that communicates with a vacuum system during operation of the interventional catheter assembly for withdrawing fluid and obstructive material through the aspiration lumen; and
   (e) an elongated cylindrical bushing extending proximally through a distal portion of the guidewire lumen, the elongated cylindrical bushing extending from a distal end positioned at a distal region of the operating head proximally through the operating head and having a proximal end terminating at a proximal end of the operating head; wherein an entire inner surface of the elongated cylindrical bushing is smaller than the guidewire lumen, thereby reducing the guidewire clearance along a length between the distal and proximal ends of the elongated cylindrical bushing during operation of the interventional catheter assembly over a guidewire.

2. The interventional catheter assembly of claim 1, wherein the guidewire lumen terminates at a guidewire exit port and the elongated cylindrical hushing terminates at a point proximal to the guidewire exit port.

3. The interventional catheter assembly of claim 1, wherein the elongated cylindrical bushing is dimensioned to provide clearance of less than about 0.005" between an internal bushing surface and a recommended guidewire surface.

4. The interventional catheter assembly of claim 1, wherein the elongated cylindrical bushing is dimensioned to provide clearance of between about 0.0015" and 0.0005" between an internal bushing surface and a recommended guidewire surface.

5. The interventional catheter assembly of claim 1, further comprising at least one infusion port in proximity to the operating head communicating with an infusion lumen for the infusion of fluids.

6. The interventional catheter assembly of claim 1, wherein the elongated cylindrical bushing has regions having different dimensions along its length.

7. The interventional catheter assembly of claim 1, wherein the elongated cylindrical bushing has an enlarged outer diameter distal region and a smaller outer diameter proximal region.

8. The interventional catheter assembly of claim 1, wherein an inner diameter of the elongated cylindrical bushing is substantially constant along its length.

9. The interventional catheter assembly of claim 1, wherein the elongated cylindrical bushing is formed from polyimide.

10. An interventional catheter assembly comprising:
    (a) an elongated tubular catheter for navigation within a patient's body;
    (b) an operating head positioned at a distal end of the catheter;
    (c) a guidewire lumen extending through the catheter and the operating head;
    (d) an aspiration lumen that communicates with a vacuum system during operation of the interventional catheter assembly for withdrawing fluid and obstructive material from an area in proximity to the operating head through the aspiration lumen; and
    (e) an elongated cylindrical bushing extending through a distal portion of the guidewire lumen, the elongated cylindrical bushing extending from a distal region of the operating head proximally through the operating head and terminating at a proximal end of the operating head; wherein an entire inner surface of the elongated cylindrical bushing is smaller than the guidewire lumen, thereby reducing the guidewire clearance along a length of the elongated cylindrical bushing during operation of the interventional catheter assembly over a guidewire.

11. The interventional catheter assembly of claim 10, additionally comprising at least one aspiration port in communication with the aspiration lumen.

12. The interventional catheter assembly of claim 10, further comprising at least one infusion port in proximity to the operating head communicating with an infusion lumen for the infusion of fluids.

13. The interventional catheter assembly of claim 10, wherein the elongated cylindrical bushing has regions having different dimensions along its length.

14. The interventional catheter assembly of claim 10, wherein the elongated cylindrical bushing has an enlarged outer diameter distal region and a smaller outer diameter proximal region.

15. The interventional catheter assembly of claim 10, wherein the elongated cylindrical bushing has an enlarged diameter region formed by providing a larger diameter tube overlying an outer surface of a tubular structure forming the bushing.

16. The interventional catheter assembly of claim 10, wherein the length of the elongated cylindrical bushing is less than 2 inches.

\* \* \* \* \*

UNITED STATES PATENT AND TRADEMARK OFFICE
CERTIFICATE OF CORRECTION

| | | |
|---|---|---|
| PATENT NO. | : 8,394,078 B2 | Page 1 of 1 |
| APPLICATION NO. | : 12/776269 | |
| DATED | : March 12, 2013 | |
| INVENTOR(S) | : Torrance et al. | |

It is certified that error appears in the above-identified patent and that said Letters Patent is hereby corrected as shown below:

IN THE SPECIFICATION:

In Column 8, Lines 54-55, delete "control module 12." and insert -- console unit 12. --, therefor.
In Column 8, Line 62, delete "16" and insert -- 14 --, therefor.
In Column 12, Line 60, delete "(FIGS. 8)" and insert -- (FIG. 8) --, therefor.

IN THE CLAIMS:
In Column 15, Line 46, in Claim 2, delete "hushing" and insert -- bushing --, therefor.

Signed and Sealed this
Eleventh Day of June, 2013

Teresa Stanek Rea
*Acting Director of the United States Patent and Trademark Office*